United States Patent
Paul, Jr. et al.

(10) Patent No.: US 8,252,017 B2
(45) Date of Patent: Aug. 28, 2012

(54) INVERTIBLE FILTER FOR EMBOLIC PROTECTION

(75) Inventors: Ram H. Paul, Jr., Bloomington, IN (US); John A. Brumleve, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 750 days.

(21) Appl. No.: 11/580,546

(22) Filed: Oct. 13, 2006

(65) Prior Publication Data
US 2007/0112374 A1  May 17, 2007

Related U.S. Application Data

(60) Provisional application No. 60/727,720, filed on Oct. 18, 2005.

(51) Int. Cl.
*A61M 29/00* (2006.01)
(52) U.S. Cl. .......................................... 606/200
(58) Field of Classification Search ............. 606/200, 606/191, 155, 213, 215, 110–115, 127, 128, 606/108, 106, 107; 623/1.12, 1.11; 600/585, 600/434
See application file for complete search history.

(56) References Cited

U.S. PATENT DOCUMENTS

| | | | |
|---|---|---|---|
| 3,108,593 A | 10/1963 | Glassman | |
| 3,334,629 A | 8/1967 | Cohn | |
| 3,472,230 A | 10/1969 | Fogarty | |
| 3,547,103 A | 12/1970 | Cook | |
| 3,635,223 A | 1/1972 | Klieman | |
| 3,923,065 A | 12/1975 | Nozick et al. | |
| 3,952,747 A | 4/1976 | Kimmell, Jr. | |
| 3,978,863 A | 9/1976 | Fettel et al. | |
| 3,996,938 A | 12/1976 | Clark, III | |
| 4,425,908 A | 1/1984 | Simon | |
| 4,456,000 A | 6/1984 | Schjeldahl et al. | |
| 4,494,531 A | 1/1985 | Gianturco | |
| 4,548,206 A | 10/1985 | Osborne | |
| 4,561,439 A | 12/1985 | Bishop et al. | |
| 4,562,039 A | 12/1985 | Koehler | |
| 4,604,094 A | 8/1986 | Shook | |
| 4,619,246 A | 10/1986 | Molgaard-Nielsen et al. | |

(Continued)

FOREIGN PATENT DOCUMENTS

DE  3429850 A1  2/1986

(Continued)

OTHER PUBLICATIONS

International Preliminary Examination Authority, PCT Notification of Transmittal of the International Preliminary Report on Patentability, 10 pgs.

(Continued)

*Primary Examiner* — Kathleen Sonnett
*Assistant Examiner* — Jocelin Tanner
(74) *Attorney, Agent, or Firm* — Brinks Hofer Gilson & Lione (57) ABSTRACT

A medical device including a guiding member and a filter portion is disclosed. The guiding member includes a lumen configured to slidably engage the filter portion. The filter portion forms a tubular geometry that extends distally from the guiding member. The filter portion is configured to evert to form a proximally facing concave geometry for capturing emboli. Further, the filter portion includes filter openings that are sized to allow blood cells to pass therethrough while preventing the passage of emboli.

13 Claims, 5 Drawing Sheets

U.S. PATENT DOCUMENTS

| | | |
|---|---|---|
| 4,643,184 A | 2/1987 | Mobin-Uddin |
| 4,646,736 A | 3/1987 | Auth |
| 4,650,472 A | 3/1987 | Bates |
| 4,665,906 A | 5/1987 | Jervis |
| 4,669,464 A | 6/1987 | Sulepov |
| 4,688,553 A | 8/1987 | Metals |
| 4,723,549 A | 2/1988 | Wholey et al. |
| 4,727,873 A | 3/1988 | Mobin-Uddin |
| 4,732,152 A | 3/1988 | Wallsten et al. |
| 4,817,600 A | 4/1989 | Herms et al. |
| 4,824,435 A | 4/1989 | Giesy et al. |
| 4,832,055 A | 5/1989 | Palestrant |
| 4,846,794 A | 7/1989 | Hertzer |
| 4,848,343 A | 7/1989 | Wallsten et al. |
| 4,873,978 A | 10/1989 | Ginsburg |
| 4,943,297 A | 7/1990 | Saveliev et al. |
| 4,957,501 A | 9/1990 | Lahille et al. |
| 4,990,156 A | 2/1991 | Lefebvre |
| 4,998,916 A | 3/1991 | Hammerslag et al. |
| 5,053,008 A * | 10/1991 | Bajaj ............................ 604/104 |
| 5,059,205 A | 10/1991 | El-Nounou et al. |
| 5,069,226 A | 12/1991 | Yamauchi et al. |
| 5,078,726 A | 1/1992 | Kreamer |
| 5,100,423 A | 3/1992 | Fearnot |
| 5,108,418 A | 4/1992 | Lefebvre |
| 5,108,419 A | 4/1992 | Reger et al. |
| 5,112,347 A | 5/1992 | Taheri |
| 5,129,890 A | 7/1992 | Bates et al. |
| 5,133,733 A | 7/1992 | Rasmussen et al. |
| 5,147,379 A | 9/1992 | Sabbaghian et al. |
| 5,152,777 A | 10/1992 | Goldberg |
| 5,160,342 A | 11/1992 | Reger |
| 5,163,927 A | 11/1992 | Woker et al. |
| 5,203,772 A | 4/1993 | Hammerslag et al. |
| 5,234,458 A | 8/1993 | Metais |
| 5,242,462 A | 9/1993 | El-Nounou |
| 5,243,996 A | 9/1993 | Hall |
| 5,251,640 A | 10/1993 | Osborne |
| 5,263,964 A | 11/1993 | Purdy |
| 5,300,086 A | 4/1994 | Gory et al. |
| 5,324,304 A | 6/1994 | Rasmussen |
| 5,329,942 A | 7/1994 | Gunther et al. |
| 5,344,427 A | 9/1994 | Cottenceau et al. |
| 5,350,397 A | 9/1994 | Palermo et al. |
| 5,350,398 A | 9/1994 | Pavcnik et al. |
| 5,364,345 A | 11/1994 | Lowery et al. |
| 5,370,657 A | 12/1994 | Irie |
| 5,375,612 A | 12/1994 | Cottenceau et al. |
| 5,383,887 A | 1/1995 | Nadal |
| 5,413,586 A | 5/1995 | Dibie et al. |
| 5,415,630 A | 5/1995 | Gory et al. |
| 5,417,708 A | 5/1995 | Hall et al. |
| 5,451,233 A | 9/1995 | Yock |
| 5,458,573 A | 10/1995 | Summers |
| 5,522,881 A | 6/1996 | Lentz |
| 5,527,338 A | 6/1996 | Purdy |
| 5,531,788 A | 7/1996 | Dibie et al. |
| 5,549,551 A | 8/1996 | Peacock et al. |
| 5,549,626 A | 8/1996 | Miller et al. |
| 5,556,414 A | 9/1996 | Turi |
| 5,562,698 A | 10/1996 | Parker |
| 5,571,135 A | 11/1996 | Fraser et al. |
| 5,591,195 A | 1/1997 | Taheri et al. |
| 5,601,595 A | 2/1997 | Smith |
| 5,624,461 A | 4/1997 | Mariant |
| 5,626,605 A | 5/1997 | Irie et al. |
| 5,630,797 A | 5/1997 | Diedrich et al. |
| 5,634,942 A | 6/1997 | Chevillon et al. |
| 5,649,953 A | 7/1997 | Lefebvre |
| 5,662,703 A | 9/1997 | Yurek et al. |
| 5,669,933 A | 9/1997 | Simon et al. |
| 5,681,347 A | 10/1997 | Cathcart et al. |
| 5,690,642 A | 11/1997 | Osborne et al. |
| 5,690,667 A | 11/1997 | Gia |
| 5,693,067 A | 12/1997 | Purdy |
| 5,693,087 A | 12/1997 | Parodi |
| 5,695,518 A | 12/1997 | Laerum |
| 5,695,519 A | 12/1997 | Summers et al. |
| 5,700,253 A | 12/1997 | Parker |
| 5,709,704 A | 1/1998 | Nott et al. |
| 5,713,853 A | 2/1998 | Clark et al. |
| 5,720,764 A | 2/1998 | Naderlinger |
| 5,725,550 A | 3/1998 | Nadal |
| 5,738,667 A | 4/1998 | Solar |
| 5,746,767 A | 5/1998 | Smith |
| 5,755,772 A | 5/1998 | Evans et al. |
| 5,755,790 A | 5/1998 | Chevillon et al. |
| 5,766,203 A | 6/1998 | Imran et al. |
| 5,769,816 A | 6/1998 | Barbut et al. |
| 5,769,871 A | 6/1998 | Mers et al. |
| 5,795,322 A | 8/1998 | Boudewijn |
| 5,800,457 A | 9/1998 | Gelbfish et al. |
| 5,800,525 A | 9/1998 | Bachinski et al. |
| 5,810,874 A | 9/1998 | Lefebvre |
| 5,814,027 A | 9/1998 | Hassett et al. |
| 5,814,064 A | 9/1998 | Daniel et al. |
| 5,820,592 A | 10/1998 | Hammerslag |
| 5,827,324 A | 10/1998 | Cassell et al. |
| 5,830,230 A | 11/1998 | Berryman et al. |
| 5,836,968 A | 11/1998 | Simon et al. |
| 5,836,969 A | 11/1998 | Kim et al. |
| 5,846,260 A | 12/1998 | Maahs |
| 5,853,420 A | 12/1998 | Chevillon et al. |
| 5,876,367 A | 3/1999 | Kaganov et al. |
| 5,893,869 A | 4/1999 | Barnhart et al. |
| 5,895,391 A | 4/1999 | Farnholtz |
| 5,895,399 A | 4/1999 | Barbut et al. |
| 5,895,410 A | 4/1999 | Forber et al. |
| 5,908,435 A | 6/1999 | Samuels |
| 5,910,154 A | 6/1999 | Tsugita et al. |
| 5,911,702 A | 6/1999 | Romley et al. |
| 5,911,704 A | 6/1999 | Humes |
| 5,911,717 A | 6/1999 | Jacobsen et al. |
| 5,911,734 A | 6/1999 | Tsugita et al. |
| 5,919,224 A | 7/1999 | Thompson et al. |
| 5,925,062 A | 7/1999 | Purdy |
| 5,925,063 A | 7/1999 | Khosravi |
| 5,928,260 A | 7/1999 | Chin et al. |
| 5,928,261 A | 7/1999 | Ruiz |
| 5,938,683 A | 8/1999 | Lefebvre |
| 5,941,896 A | 8/1999 | Kerr |
| 5,944,728 A | 8/1999 | Bates |
| 5,947,985 A | 9/1999 | Imran |
| 5,947,995 A | 9/1999 | Samuels |
| 5,948,017 A | 9/1999 | Taheri |
| 5,951,567 A | 9/1999 | Javier, Jr. et al. |
| 5,954,741 A | 9/1999 | Fox |
| 5,954,742 A | 9/1999 | Osypka |
| 5,954,745 A | 9/1999 | Gertler et al. |
| 5,968,057 A | 10/1999 | Taheri |
| 5,968,071 A | 10/1999 | Chevillon et al. |
| 5,972,019 A | 10/1999 | Engelson et al. |
| 5,976,162 A | 11/1999 | Doan et al. |
| 5,976,172 A | 11/1999 | Homsma et al. |
| 5,980,555 A | 11/1999 | Barbut et al. |
| 5,984,947 A | 11/1999 | Smith |
| 5,984,965 A | 11/1999 | Knapp et al. |
| 5,989,281 A | 11/1999 | Barbut et al. |
| 6,001,118 A | 12/1999 | Daniel et al. |
| 6,007,557 A | 12/1999 | Ambrisco et al. |
| 6,007,558 A | 12/1999 | Ravenscloth et al. |
| 6,010,522 A | 1/2000 | Barbut et al. |
| 6,013,093 A | 1/2000 | Nott et al. |
| 6,015,424 A | 1/2000 | Rosenbluth et al. |
| 6,027,520 A | 2/2000 | Tsugita et al. |
| 6,036,717 A | 3/2000 | Mers Kelly et al. |
| 6,036,720 A | 3/2000 | Abrams et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,745 A | 5/2000 | Gelbfish |
| 6,059,813 A | 5/2000 | Vrba et al. |
| 6,059,814 A | 5/2000 | Ladd |
| 6,063,113 A | 5/2000 | Kavteladze et al. |
| 6,066,158 A | 5/2000 | Engelson et al. |
| 6,068,645 A | 5/2000 | Tu |

| | | | |
|---|---|---|---|
| 6,074,357 A | 6/2000 | Kaganov et al. |
| 6,077,274 A | 6/2000 | Ouchi et al. |
| 6,080,178 A | 6/2000 | Meglin |
| 6,083,239 A | 7/2000 | Addis |
| 6,086,577 A | 7/2000 | Ken et al. |
| 6,086,605 A | 7/2000 | Barbut et al. |
| 6,093,199 A | 7/2000 | Brown et al. |
| 6,096,053 A | 8/2000 | Bates |
| 6,096,070 A | 8/2000 | Ragheb et al. |
| 6,099,549 A | 8/2000 | Bosma et al. |
| 6,106,497 A | 8/2000 | Wang |
| 6,126,672 A | 10/2000 | Berryman et al. |
| 6,126,673 A | 10/2000 | Kim et al. |
| 6,129,739 A | 10/2000 | Khosravi |
| 6,136,016 A | 10/2000 | Barbut et al. |
| 6,146,396 A | 11/2000 | Konya et al. |
| 6,146,404 A | 11/2000 | Kim et al. |
| 6,152,931 A | 11/2000 | Nadal et al. |
| 6,152,946 A | 11/2000 | Broome et al. |
| 6,152,947 A | 11/2000 | Ambrisco et al. |
| 6,156,061 A | 12/2000 | Wallace et al. |
| 6,156,062 A | 12/2000 | McGuinness |
| 6,159,230 A | 12/2000 | Samuels |
| 6,165,179 A | 12/2000 | Cathcart et al. |
| 6,165,198 A | 12/2000 | McGurk et al. |
| 6,165,199 A | 12/2000 | Barbut |
| 6,165,200 A | 12/2000 | Tsugita et al. |
| 6,168,579 B1 | 1/2001 | Tsugita et al. |
| 6,168,603 B1 | 1/2001 | Leslie et al. |
| 6,168,610 B1 | 1/2001 | Marin et al. |
| 6,168,622 B1 | 1/2001 | Mazzocchi |
| 6,171,327 B1 | 1/2001 | Daniel et al. |
| 6,171,328 B1 | 1/2001 | Addis |
| 6,174,318 B1 | 1/2001 | Bates et al. |
| 6,179,851 B1 | 1/2001 | Barbut et al. |
| 6,179,859 B1 | 1/2001 | Bates et al. |
| 6,179,860 B1 | 1/2001 | Fulton, III et al. |
| 6,179,861 B1 | 1/2001 | Khosravi et al. |
| 6,187,025 B1 | 2/2001 | Machek |
| 6,193,739 B1 | 2/2001 | Chevillon et al. |
| 6,203,561 B1 | 3/2001 | Ramee et al. |
| 6,206,931 B1 | 3/2001 | Cook et al. |
| 6,214,025 B1 | 4/2001 | Thistle et al. |
| 6,214,026 B1 | 4/2001 | Lepak et al. |
| 6,221,091 B1 | 4/2001 | Khosravi |
| 6,224,620 B1 | 5/2001 | Maahs |
| 6,231,588 B1 | 5/2001 | Zadno-Azizi |
| 6,231,589 B1 | 5/2001 | Wessman et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,012 B1 | 6/2001 | Kleshinski |
| 6,245,087 B1 | 6/2001 | Addis |
| 6,245,088 B1 * | 6/2001 | Lowery .................. 606/200 |
| 6,245,089 B1 | 6/2001 | Daniel et al. |
| 6,251,092 B1 | 6/2001 | Qin et al. |
| 6,251,122 B1 | 6/2001 | Tsukernik |
| 6,254,550 B1 | 7/2001 | McNamara et al. |
| 6,254,633 B1 | 7/2001 | Pinchuk et al. |
| 6,258,026 B1 | 7/2001 | Ravenscroft et al. |
| 6,258,115 B1 | 7/2001 | Dubrul |
| 6,258,120 B1 | 7/2001 | McKenzie et al. |
| 6,261,305 B1 | 7/2001 | Marotta et al. |
| 6,264,672 B1 | 7/2001 | Fisher |
| 6,267,776 B1 | 7/2001 | O'Connell |
| 6,267,777 B1 | 7/2001 | Bosma et al. |
| 6,273,900 B1 | 8/2001 | Nott et al. |
| 6,273,901 B1 | 8/2001 | Whitcher et al. |
| 6,277,125 B1 | 8/2001 | Barry et al. |
| 6,277,126 B1 | 8/2001 | Barry et al. |
| 6,277,138 B1 | 8/2001 | Levinson et al. |
| 6,277,139 B1 | 8/2001 | Levinson et al. |
| 6,280,451 B1 | 8/2001 | Bates et al. |
| 6,287,321 B1 | 9/2001 | Jang |
| 6,290,710 B1 | 9/2001 | Cryer et al. |
| 6,299,604 B1 | 10/2001 | Ragheb et al. |
| 6,306,163 B1 | 10/2001 | Fitz |
| 6,309,399 B1 | 10/2001 | Barbut et al. |
| 6,312,444 B1 | 11/2001 | Barbut |
| 6,319,268 B1 | 11/2001 | Ambrisco et al. |
| 6,325,815 B1 | 12/2001 | Kusleika et al. |
| 6,325,816 B1 | 12/2001 | Fulton, III et al. |
| 6,328,755 B1 | 12/2001 | Marshall |
| 6,331,183 B1 | 12/2001 | Suon |
| 6,331,184 B1 | 12/2001 | Abrams |
| 6,334,864 B1 | 1/2002 | Amplatz et al. |
| 6,336,934 B1 | 1/2002 | Gilson et al. |
| 6,338,739 B1 | 1/2002 | Datta et al. |
| 6,340,364 B2 | 1/2002 | Kanesaka |
| 6,342,062 B1 | 1/2002 | Suon et al. |
| 6,342,063 B1 | 1/2002 | DeVries et al. |
| 6,344,048 B1 | 2/2002 | Chin et al. |
| 6,344,049 B1 | 2/2002 | Levinson et al. |
| 6,346,116 B1 | 2/2002 | Brooks et al. |
| 6,348,041 B1 | 2/2002 | Klint |
| 6,348,063 B1 | 2/2002 | Yassour et al. |
| 6,350,271 B1 | 2/2002 | Kurz et al. |
| 6,355,051 B1 | 3/2002 | Sisskind et al. |
| 6,358,228 B1 | 3/2002 | Tubman et al. |
| 6,361,545 B1 | 3/2002 | Macoviak et al. |
| 6,361,546 B1 | 3/2002 | Khosravi |
| 6,361,547 B1 | 3/2002 | Hieshima |
| 6,364,895 B1 | 4/2002 | Greenhalgh |
| 6,364,896 B1 | 4/2002 | Addis |
| 6,368,338 B1 | 4/2002 | Konya et al. |
| 6,371,961 B1 | 4/2002 | Osborne et al. |
| 6,371,969 B1 | 4/2002 | Tsugita et al. |
| 6,371,970 B1 | 4/2002 | Khosravi et al. |
| 6,371,971 B1 | 4/2002 | Tsugita et al. |
| 6,375,670 B1 | 4/2002 | Greenhalgh |
| 6,379,374 B1 | 4/2002 | Hieshima et al. |
| 6,380,457 B1 | 4/2002 | Yurek et al. |
| 6,383,146 B1 | 5/2002 | Klint |
| 6,383,171 B1 | 5/2002 | Gifford et al. |
| 6,383,174 B1 | 5/2002 | Eder |
| 6,383,193 B1 | 5/2002 | Cathcart et al. |
| 6,383,196 B1 | 5/2002 | Leslie et al. |
| 6,383,205 B1 | 5/2002 | Samson et al. |
| 6,383,206 B1 | 5/2002 | Gillick et al. |
| 6,391,044 B1 | 5/2002 | Yadav et al. |
| 6,391,045 B1 | 5/2002 | Kim et al. |
| 6,391,052 B2 | 5/2002 | Buirge et al. |
| 6,395,014 B1 | 5/2002 | Macoviak et al. |
| 6,402,771 B1 | 6/2002 | Palmer et al. |
| 6,402,772 B1 | 6/2002 | Amplatz et al. |
| 6,409,742 B1 | 6/2002 | Fulton, III et al. |
| 6,413,235 B1 | 7/2002 | Parodi |
| 6,416,530 B2 | 7/2002 | DeVries et al. |
| 6,419,686 B1 | 7/2002 | McLeod et al. |
| 6,423,052 B1 | 7/2002 | Escano |
| 6,423,086 B1 | 7/2002 | Barbut et al. |
| 6,425,909 B1 | 7/2002 | Dieck et al. |
| 6,428,557 B1 | 8/2002 | Hilaire |
| 6,428,558 B1 | 8/2002 | Jones et al. |
| 6,428,559 B1 | 8/2002 | Johnson |
| 6,432,122 B1 | 8/2002 | Gilson et al. |
| 6,436,112 B2 | 8/2002 | Wensel et al. |
| 6,436,120 B1 | 8/2002 | Meglin |
| 6,436,121 B1 | 8/2002 | Blom |
| 6,443,926 B1 | 9/2002 | Kletschka |
| 6,443,971 B1 | 9/2002 | Boylan et al. |
| 6,443,972 B1 | 9/2002 | Bosma et al. |
| 6,443,979 B1 | 9/2002 | Stalker et al. |
| 6,447,530 B1 | 9/2002 | Ostrovsky et al. |
| 6,447,531 B1 | 9/2002 | Amplatz |
| 6,454,775 B1 | 9/2002 | Demarais et al. |
| 6,458,139 B1 | 10/2002 | Palmer et al. |
| 6,458,145 B1 | 10/2002 | Ravenscroft et al. |
| 6,461,370 B1 | 10/2002 | Gray et al. |
| 6,468,290 B1 | 10/2002 | Weldon et al. |
| 6,468,291 B2 | 10/2002 | Bates et al. |
| 6,482,222 B1 | 11/2002 | Bruckheimer et al. |
| 6,485,456 B1 | 11/2002 | Kletschka |
| 6,485,500 B1 | 11/2002 | Kokish et al. |
| 6,485,501 B1 | 11/2002 | Green |
| 6,485,502 B2 | 11/2002 | Don Michael et al. |
| 6,491,712 B1 | 12/2002 | O'Connor |

| Patent | Type | Date | Inventor |
|---|---|---|---|
| 6,494,895 | B2 | 12/2002 | Addis |
| 6,497,709 | B1 | 12/2002 | Heath |
| 6,499,487 | B1 | 12/2002 | McKenzie et al. |
| 6,500,166 | B1 | 12/2002 | Zadno Azizi et al. |
| 6,500,191 | B2 | 12/2002 | Addis |
| 6,502,606 | B2 | 1/2003 | Klint |
| 6,506,203 | B1 | 1/2003 | Boyle et al. |
| 6,506,205 | B2 | 1/2003 | Goldberg et al. |
| 6,508,826 | B2 | 1/2003 | Murphy et al. |
| 6,511,492 | B1 | 1/2003 | Rosenbluth et al. |
| 6,511,496 | B1 | 1/2003 | Huter et al. |
| 6,511,497 | B1 | 1/2003 | Braun et al. |
| 6,511,503 | B1 | 1/2003 | Burkett et al. |
| 6,514,273 | B1 | 2/2003 | Voss et al. |
| 6,517,559 | B1 | 2/2003 | O'Connell |
| 6,520,978 | B1 | 2/2003 | Blackledge et al. |
| 6,520,983 | B1 | 2/2003 | Colgan et al. |
| 6,527,746 | B1 | 3/2003 | Oslund et al. |
| 6,527,791 | B2 | 3/2003 | Fisher |
| 6,527,962 | B1 | 3/2003 | Nadal |
| 6,530,935 | B2 | 3/2003 | Wensel et al. |
| 6,530,939 | B1 | 3/2003 | Hopkins et al. |
| 6,530,940 | B2 | 3/2003 | Fisher |
| 6,533,770 | B1 | 3/2003 | Lepulu et al. |
| 6,533,800 | B1 | 3/2003 | Barbut |
| 6,537,293 | B1 | 3/2003 | Berryman et al. |
| 6,537,294 | B1 | 3/2003 | Boyle et al. |
| 6,537,296 | B2 | 3/2003 | Levinson et al. |
| 6,537,297 | B2 | 3/2003 | Tsugita et al. |
| 6,540,722 | B1 | 4/2003 | Boyle et al. |
| 6,540,767 | B1 | 4/2003 | Walak et al. |
| 6,540,768 | B1 | 4/2003 | Diaz et al. |
| 6,544,221 | B1 | 4/2003 | Kokish et al. |
| 6,544,276 | B1 | 4/2003 | Azizi |
| 6,544,278 | B1 | 4/2003 | Vrba et al. |
| 6,544,279 | B1 | 4/2003 | Hopkins et al. |
| 6,544,280 | B1 | 4/2003 | Daniel et al. |
| 6,547,759 | B1 | 4/2003 | Fisher |
| 6,551,303 | B1 | 4/2003 | Van Tassel et al. |
| 6,551,341 | B2 | 4/2003 | Boylan et al. |
| 6,551,342 | B1 | 4/2003 | Shen et al. |
| 6,554,849 | B1 | 4/2003 | Jones et al. |
| 6,558,404 | B2 | 5/2003 | Tsukernik |
| 6,558,405 | B1 | 5/2003 | McInnes |
| 6,558,406 | B2 | 5/2003 | Okada |
| 6,562,058 | B2 | 5/2003 | Seguin et al. |
| 6,565,591 | B2 | 5/2003 | Brady et al. |
| 6,569,147 | B1 | 5/2003 | Evans et al. |
| 6,569,183 | B1 | 5/2003 | Kim et al. |
| 6,569,184 | B2 | 5/2003 | Huter |
| 6,575,995 | B1 | 6/2003 | Huter et al. |
| 6,575,996 | B1 | 6/2003 | Denison et al. |
| 6,575,997 | B1 | 6/2003 | Palmer et al. |
| 6,579,303 | B2 | 6/2003 | Amplatz |
| 6,582,396 | B1 | 6/2003 | Parodi |
| 6,582,447 | B1 | 6/2003 | Patel et al. |
| 6,582,448 | B1 | 6/2003 | Boyle et al. |
| 6,589,227 | B2 | 7/2003 | Klint |
| 6,589,230 | B2 | 7/2003 | Gia et al. |
| 6,589,263 | B1 | 7/2003 | Hopkins et al. |
| 6,589,264 | B1 | 7/2003 | Barbut et al. |
| 6,589,265 | B1 | 7/2003 | Palmer et al. |
| 6,589,266 | B2 | 7/2003 | Whitcher et al. |
| 6,592,546 | B1 | 7/2003 | Barbut et al. |
| 6,592,606 | B2 | 7/2003 | Huter et al. |
| 6,592,616 | B1 | 7/2003 | Stack et al. |
| 6,595,983 | B2 | 7/2003 | Voda |
| 6,596,011 | B2 | 7/2003 | Johnson et al. |
| 6,599,275 | B1 | 7/2003 | Fischer, Jr. |
| 6,599,307 | B1 | 7/2003 | Huter et al. |
| 6,599,308 | B2 | 7/2003 | Amplatz |
| 6,602,271 | B2 | 8/2003 | Adams et al. |
| 6,602,273 | B2 | 8/2003 | Marshall |
| 6,602,280 | B2 | 8/2003 | Chobotov |
| 6,605,102 | B1 | 8/2003 | Mazzocchi et al. |
| 6,607,506 | B2 | 8/2003 | Kletschka |
| 6,610,077 | B1 | 8/2003 | Hancock et al. |
| 6,611,720 | B2 | 8/2003 | Hata et al. |
| 6,613,074 | B1 | 9/2003 | Mitelberg et al. |
| 6,616,679 | B1 | 9/2003 | Khosravi et al. |
| 6,616,680 | B1 | 9/2003 | Thielen |
| 6,616,681 | B2 | 9/2003 | Hanson et al. |
| 6,616,682 | B2 | 9/2003 | Joergensen et al. |
| 6,620,148 | B1 | 9/2003 | Tsugita |
| 6,620,182 | B1 | 9/2003 | Khosravi et al. |
| 6,623,450 | B1 | 9/2003 | Dutta |
| 6,623,506 | B2 | 9/2003 | McGuckin, Jr. et al. |
| 6,629,953 | B1 | 10/2003 | Boyd |
| 6,635,068 | B1 | 10/2003 | Dubrul et al. |
| 6,635,069 | B1 | 10/2003 | Teoh et al. |
| 6,635,070 | B2 * | 10/2003 | Leeflang et al. ............... 606/200 |
| 6,638,293 | B1 | 10/2003 | Makower et al. |
| 6,638,294 | B1 | 10/2003 | Palmer |
| 6,638,372 | B1 | 10/2003 | Abrams et al. |
| 6,641,590 | B1 | 11/2003 | Palmer et al. |
| 6,641,605 | B1 | 11/2003 | Stergiopulos |
| 6,645,160 | B1 | 11/2003 | Heesch |
| 6,645,220 | B1 | 11/2003 | Huter et al. |
| 6,645,221 | B1 | 11/2003 | Richter |
| 6,645,222 | B1 | 11/2003 | Parodi et al. |
| 6,645,223 | B2 | 11/2003 | Boyle et al. |
| 6,645,224 | B2 | 11/2003 | Gilson et al. |
| 6,652,554 | B1 | 11/2003 | Wholey et al. |
| 6,652,557 | B1 | 11/2003 | MacDonald |
| 6,652,558 | B2 | 11/2003 | Patel et al. |
| 6,656,201 | B2 | 12/2003 | Ferrera et al. |
| 6,656,202 | B2 | 12/2003 | Papp et al. |
| 6,656,203 | B2 | 12/2003 | Roth et al. |
| 6,656,204 | B2 | 12/2003 | Ambrisco et al. |
| 6,656,351 | B2 | 12/2003 | Boyle |
| 6,660,021 | B1 | 12/2003 | Palmer et al. |
| 6,663,613 | B1 | 12/2003 | Evans et al. |
| 6,663,650 | B2 | 12/2003 | Sepetka et al. |
| 6,663,651 | B2 | 12/2003 | Krolik et al. |
| 6,663,652 | B2 | 12/2003 | Daniel et al. |
| 6,676,682 | B1 | 1/2004 | Tsugita et al. |
| 6,679,902 | B1 | 1/2004 | Boyle et al. |
| 6,689,144 | B2 | 2/2004 | Gerberding |
| 6,695,813 | B1 | 2/2004 | Boyle et al. |
| 6,695,865 | B2 | 2/2004 | Boyle et al. |
| 6,702,834 | B1 | 3/2004 | Boylan et al. |
| 6,709,450 | B2 | 3/2004 | Kang et al. |
| 6,712,835 | B2 | 3/2004 | Mazzocchi et al. |
| 6,716,207 | B2 | 4/2004 | Farnholtz |
| 6,716,231 | B1 | 4/2004 | Rafiee et al. |
| 6,726,701 | B2 | 4/2004 | Gilson et al. |
| 6,730,064 | B2 | 5/2004 | Ragheb et al. |
| 6,755,855 | B2 | 6/2004 | Yurek et al. |
| 6,755,856 | B2 | 6/2004 | Fierens et al. |
| 6,758,855 | B2 | 7/2004 | Fulton, III et al. |
| 6,761,727 | B1 | 7/2004 | Ladd |
| 6,773,446 | B1 | 8/2004 | Dwyer et al. |
| 6,773,448 | B2 | 8/2004 | Kusleika et al. |
| 6,774,278 | B1 | 8/2004 | Ragheb et al. |
| 6,780,175 | B1 | 8/2004 | Sachdeva et al. |
| 6,793,667 | B2 | 9/2004 | Hebert et al. |
| 6,793,668 | B1 | 9/2004 | Fisher |
| 6,833,002 | B2 | 12/2004 | Stack et al. |
| 6,855,154 | B2 | 2/2005 | Abdel-Gawwad |
| 6,866,677 | B2 | 3/2005 | Douk et al. |
| 6,866,680 | B2 | 3/2005 | Yassour et al. |
| 6,872,211 | B2 | 3/2005 | White et al. |
| 6,878,153 | B2 | 4/2005 | Linder et al. |
| 6,896,691 | B2 | 5/2005 | Boylan et al. |
| 6,929,709 | B2 | 8/2005 | Smith |
| 6,932,831 | B2 | 8/2005 | Forber |
| 6,936,059 | B2 | 8/2005 | Belef |
| 6,939,361 | B1 | 9/2005 | Kleshinski |
| 6,942,682 | B2 | 9/2005 | Vrba et al. |
| 6,955,685 | B2 | 10/2005 | Escamilla et al. |
| 6,964,670 | B1 | 11/2005 | Shah et al. |
| 6,964,674 | B1 * | 11/2005 | Matsuura et al. ............. 606/213 |
| 6,969,396 | B2 | 11/2005 | Krolik et al. |
| 6,974,469 | B2 | 12/2005 | Broome et al. |
| 6,974,473 | B2 | 12/2005 | Barclay et al. |
| 6,986,784 | B1 | 1/2006 | Weiser et al. |
| 6,991,641 | B2 | 1/2006 | Diaz et al. |
| 7,128,073 | B1 | 10/2006 | Van Der Burg et al. |

| | | | | | |
|---|---|---|---|---|---|
| 7,166,120 B2 * | 1/2007 | Kusleika ............... 606/191 | 2002/0095173 A1 | 7/2002 | Mazzocchi et al. |
| 7,174,636 B2 | 2/2007 | Lowe | 2002/0095174 A1 | 7/2002 | Tsugita et al. |
| 7,189,249 B2 | 3/2007 | Hart et al. | 2002/0099405 A1 | 7/2002 | Yurek et al. |
| 7,204,847 B1 | 4/2007 | Gambale | 2002/0099407 A1 | 7/2002 | Becker et al. |
| 7,220,271 B2 | 5/2007 | Clubb et al. | 2002/0099435 A1 | 7/2002 | Stinson |
| 7,255,687 B2 | 8/2007 | Huang et al. | 2002/0103501 A1 | 8/2002 | Diaz et al. |
| 7,285,130 B2 | 10/2007 | Austin | 2002/0107541 A1 | 8/2002 | Vale et al. |
| 7,306,619 B1 | 12/2007 | Palmer | 2002/0111647 A1 | 8/2002 | Khairkhahan et al. |
| 7,371,248 B2 | 5/2008 | Dapolito et al. | 2002/0111648 A1 | 8/2002 | Kusleika et al. |
| 7,393,358 B2 | 7/2008 | Malewicz | 2002/0111649 A1 | 8/2002 | Russo et al. |
| 7,604,649 B2 | 10/2009 | McGuckin et al. | 2002/0116024 A1 | 8/2002 | Goldberg et al. |
| 7,666,216 B2 | 2/2010 | Hogendijk et al. | 2002/0120226 A1 | 8/2002 | Beck |
| 7,731,722 B2 | 6/2010 | Lavelle et al. | 2002/0120286 A1 | 8/2002 | DoBrava et al. |
| 7,766,934 B2 | 8/2010 | Pal et al. | 2002/0120287 A1 | 8/2002 | Huter |
| 2001/0000799 A1 | 5/2001 | Wessman et al. | 2002/0123720 A1 | 9/2002 | Kusleika et al. |
| 2001/0001817 A1 | 5/2001 | Humes | 2002/0123755 A1 | 9/2002 | Lowe et al. |
| 2001/0005789 A1 | 6/2001 | Root et al. | 2002/0123759 A1 | 9/2002 | Amplatz |
| 2001/0007947 A1 | 7/2001 | Kanesaka | 2002/0123766 A1 | 9/2002 | Seguin et al. |
| 2001/0011181 A1 | 8/2001 | DiMatteo | 2002/0128679 A1 | 9/2002 | Turovskiy et al. |
| 2001/0011182 A1 | 8/2001 | Dubrul et al. | 2002/0128680 A1 | 9/2002 | Pavlovic |
| 2001/0012951 A1 | 8/2001 | Bates et al. | 2002/0128681 A1 | 9/2002 | Broome et al. |
| 2001/0016755 A1 | 8/2001 | Addis | 2002/0133191 A1 | 9/2002 | Khosravi et al. |
| 2001/0020175 A1 | 9/2001 | Yassour et al. | 2002/0133192 A1 | 9/2002 | Kusleika et al. |
| 2001/0023358 A1 | 9/2001 | Tsukernik | 2002/0138094 A1 | 9/2002 | Borillo et al. |
| 2001/0025187 A1 | 9/2001 | Okada | 2002/0138095 A1 | 9/2002 | Mazzocchi et al. |
| 2001/0031980 A1 | 10/2001 | Wensel et al. | 2002/0138096 A1 | 9/2002 | Hieshima |
| 2001/0031981 A1 | 10/2001 | Evans et al. | 2002/0138097 A1 | 9/2002 | Ostrovsky et al. |
| 2001/0031982 A1 | 10/2001 | Peterson et al. | 2002/0143360 A1 | 10/2002 | Douk et al. |
| 2001/0039431 A1 | 11/2001 | DeVries et al. | 2002/0143361 A1 | 10/2002 | Douk et al. |
| 2001/0039432 A1 | 11/2001 | Whitcher et al. | 2002/0143362 A1 | 10/2002 | Macoviak et al. |
| 2001/0041908 A1 | 11/2001 | Levinson et al. | 2002/0151927 A1 | 10/2002 | Douk et al. |
| 2001/0041909 A1 | 11/2001 | Tsugita et al. | 2002/0151928 A1 | 10/2002 | Leslie et al. |
| 2001/0041928 A1 | 11/2001 | Pavcnik et al. | 2002/0156520 A1 | 10/2002 | Boylan et al. |
| 2001/0044632 A1 | 11/2001 | Daniel et al. | 2002/0161389 A1 | 10/2002 | Boyle et al. |
| 2001/0044634 A1 | 11/2001 | Don Michael et al. | 2002/0161390 A1 | 10/2002 | Mouw |
| 2001/0053921 A1 | 12/2001 | Jang | 2002/0161391 A1 | 10/2002 | Murphy et al. |
| 2002/0002383 A1 | 1/2002 | Sepetka et al. | 2002/0161392 A1 | 10/2002 | Dubrul |
| 2002/0002384 A1 | 1/2002 | Gilson et al. | 2002/0161393 A1 | 10/2002 | Demond et al. |
| 2002/0004667 A1 | 1/2002 | Adams et al. | 2002/0161394 A1 | 10/2002 | Macoviak et al. |
| 2002/0016564 A1 | 2/2002 | Courtney et al. | 2002/0161395 A1 | 10/2002 | Douk et al. |
| 2002/0016609 A1 | 2/2002 | Wensel et al. | 2002/0161396 A1 | 10/2002 | Jang et al. |
| 2002/0022858 A1 | 2/2002 | Demond et al. | 2002/0165557 A1 | 11/2002 | McAlister |
| 2002/0022859 A1 | 2/2002 | Hogendijk | 2002/0165573 A1 | 11/2002 | Barbut |
| 2002/0026211 A1 | 2/2002 | Khosravi et al. | 2002/0165576 A1 | 11/2002 | Boyle et al. |
| 2002/0026212 A1 | 2/2002 | Wholey et al. | 2002/0165598 A1 | 11/2002 | Wahr et al. |
| 2002/0026213 A1 | 2/2002 | Gilson et al. | 2002/0169472 A1 | 11/2002 | Douk et al. |
| 2002/0032460 A1 | 3/2002 | Kusleika et al. | 2002/0169474 A1 | 11/2002 | Kusleika et al. |
| 2002/0032461 A1 | 3/2002 | Marshall | 2002/0173815 A1 | 11/2002 | Hogendijk et al. |
| 2002/0042626 A1 | 4/2002 | Hanson et al. | 2002/0173819 A1 | 11/2002 | Leeflang et al. |
| 2002/0042627 A1 | 4/2002 | Brady et al. | 2002/0177872 A1 | 11/2002 | Papp et al. |
| 2002/0045915 A1 | 4/2002 | Balceta et al. | 2002/0177899 A1 | 11/2002 | Eum et al. |
| 2002/0045916 A1 | 4/2002 | Gray et al. | 2002/0183781 A1 | 12/2002 | Casey et al. |
| 2002/0045918 A1 | 4/2002 | Suon et al. | 2002/0183782 A1 | 12/2002 | Tsugita et al. |
| 2002/0049452 A1 | 4/2002 | Kurz et al. | 2002/0183783 A1 | 12/2002 | Shadduck |
| 2002/0049468 A1 | 4/2002 | Streeter et al. | 2002/0188313 A1 | 12/2002 | Johnson et al. |
| 2002/0052627 A1 | 5/2002 | Boylan et al. | 2002/0188314 A1 | 12/2002 | Anderson et al. |
| 2002/0058904 A1 | 5/2002 | Boock et al. | 2002/0193824 A1 | 12/2002 | Boylan et al. |
| 2002/0058911 A1 | 5/2002 | Gilson et al. | 2002/0193825 A1 | 12/2002 | McGuckin et al. |
| 2002/0058963 A1 | 5/2002 | Vale et al. | 2002/0193826 A1 | 12/2002 | McGuckin et al. |
| 2002/0058964 A1 | 5/2002 | Addis | 2002/0193827 A1 | 12/2002 | McGuckin et al. |
| 2002/0062133 A1 | 5/2002 | Gilson et al. | 2002/0193828 A1 | 12/2002 | Griffin et al. |
| 2002/0062134 A1 | 5/2002 | Barbut et al. | 2002/0198561 A1 | 12/2002 | Amplatz |
| 2002/0062135 A1 | 5/2002 | Mazzocchi et al. | 2003/0004536 A1 | 1/2003 | Boylan et al. |
| 2002/0065507 A1 | 5/2002 | Zadno-Azizi | 2003/0004537 A1 | 1/2003 | Boyle et al. |
| 2002/0068954 A1 | 6/2002 | Foster | 2003/0004538 A1 | 1/2003 | Secrest et al. |
| 2002/0068955 A1 | 6/2002 | Khosravi | 2003/0004539 A1 | 1/2003 | Linder et al. |
| 2002/0072764 A1 | 6/2002 | Sepetka et al. | 2003/0004540 A1 | 1/2003 | Linder et al. |
| 2002/0072765 A1 | 6/2002 | Mazzocchi et al. | 2003/0004541 A1 | 1/2003 | Linder et al. |
| 2002/0077596 A1 | 6/2002 | McKenzie et al. | 2003/0004542 A1 | 1/2003 | Wensel et al. |
| 2002/0082558 A1 | 6/2002 | Samson et al. | 2003/0009146 A1 | 1/2003 | Muni et al. |
| 2002/0082639 A1 | 6/2002 | Broome et al. | 2003/0009189 A1 | 1/2003 | Gilson et al. |
| 2002/0087187 A1 | 7/2002 | Mazzocchi et al. | 2003/0009190 A1 | 1/2003 | Kletschka et al. |
| 2002/0090389 A1 | 7/2002 | Humes et al. | 2003/0009191 A1 | 1/2003 | Wensel et al. |
| 2002/0091407 A1 | 7/2002 | Zadno-Azizi et al. | 2003/0014072 A1 | 1/2003 | Wensel et al. |
| 2002/0091408 A1 | 7/2002 | Sutton et al. | 2003/0018354 A1 | 1/2003 | Roth et al. |
| 2002/0091409 A1 | 7/2002 | Sutton et al. | 2003/0018355 A1 | 1/2003 | Goto et al. |
| 2002/0095170 A1 | 7/2002 | Krolik et al. | 2003/0023263 A1 | 1/2003 | Krolik et al. |
| 2002/0095171 A1 | 7/2002 | Belef | 2003/0023264 A1 | 1/2003 | Dieck et al. |
| 2002/0095172 A1 | 7/2002 | Mazzocchi et al. | 2003/0023265 A1 | 1/2003 | Forber |

| | | | | | |
|---|---|---|---|---|---|
| 2003/0032976 A1 | 2/2003 | Boucek | 2003/0176885 A1 | 9/2003 | Broome et al. |
| 2003/0032977 A1 | 2/2003 | Brady | 2003/0176886 A1 | 9/2003 | Wholey et al. |
| 2003/0040772 A1 | 2/2003 | Hyodoh et al. | 2003/0176887 A1 | 9/2003 | Petersen |
| 2003/0045897 A1 | 3/2003 | Huter et al. | 2003/0176888 A1 | 9/2003 | O'Connell |
| 2003/0045898 A1 | 3/2003 | Harrison et al. | 2003/0176889 A1 | 9/2003 | Boyle et al. |
| 2003/0050662 A1 | 3/2003 | Don Michael | 2003/0181942 A1 | 9/2003 | Sutton et al. |
| 2003/0055452 A1 | 3/2003 | Joergensen et al. | 2003/0181943 A1 | 9/2003 | Daniel et al. |
| 2003/0055480 A1 | 3/2003 | Fischell et al. | 2003/0717769 | 9/2003 | Barbut |
| 2003/0060843 A1 | 3/2003 | Boucher | 2003/0187474 A1 | 10/2003 | Keegan et al. |
| 2003/0060844 A1 | 3/2003 | Borillo et al. | 2003/0187475 A1 | 10/2003 | Tsugita et al. |
| 2003/0065354 A1 | 4/2003 | Boyle et al. | 2003/0187495 A1 | 10/2003 | Cully et al. |
| 2003/0065355 A1 | 4/2003 | Weber | 2003/0191492 A1 | 10/2003 | Gellman et al. |
| 2003/0065356 A1 | 4/2003 | Tsugita et al. | 2003/0191493 A1 | 10/2003 | Epstein et al. |
| 2003/0069596 A1 | 4/2003 | Eskuri | 2003/0195554 A1 | 10/2003 | Shen et al. |
| 2003/0073979 A1 | 4/2003 | Naimark et al. | 2003/0195555 A1 | 10/2003 | Khairkhahan et al. |
| 2003/0074019 A1 | 4/2003 | Gray et al. | 2003/0195556 A1 | 10/2003 | Stack et al. |
| 2003/0074054 A1 | 4/2003 | Duerig et al. | 2003/0199819 A1 | 10/2003 | Beck |
| 2003/0078614 A1 | 4/2003 | Salahieh et al. | 2003/0199917 A1 | 10/2003 | Knudson et al. |
| 2003/0083608 A1 | 5/2003 | Evans et al. | 2003/0199918 A1 | 10/2003 | Patel et al. |
| 2003/0083692 A1 | 5/2003 | Vrba et al. | 2003/0199919 A1 | 10/2003 | Palmer et al. |
| 2003/0083693 A1 | 5/2003 | Daniel et al. | 2003/0199920 A1 | 10/2003 | Boylan et al. |
| 2003/0088211 A1 | 5/2003 | Anderson et al. | 2003/0199921 A1 | 10/2003 | Palmer et al. |
| 2003/0088266 A1 | 5/2003 | Bowlin | 2003/0204168 A1 | 10/2003 | Bosma et al. |
| 2003/0093110 A1 | 5/2003 | Vale | 2003/0204202 A1 | 10/2003 | Palmer et al. |
| 2003/0093112 A1 | 5/2003 | Addis | 2003/0204203 A1 | 10/2003 | Khairkhahan et al. |
| 2003/0097094 A1 | 5/2003 | Ouriel et al. | 2003/0208222 A1 | 11/2003 | Zadno-Azizi |
| 2003/0097145 A1 | 5/2003 | Goldberg et al. | 2003/0208224 A1 | 11/2003 | Broome |
| 2003/0100917 A1 | 5/2003 | Boyle et al. | 2003/0208225 A1 | 11/2003 | Goll et al. |
| 2003/0100918 A1 | 5/2003 | Duane | 2003/0208226 A1 | 11/2003 | Bruckheimer et al. |
| 2003/0100919 A1 | 5/2003 | Hopkins et al. | 2003/0208227 A1 | 11/2003 | Thomas |
| 2003/0105472 A1 | 6/2003 | McAlister | 2003/0208228 A1 | 11/2003 | Gilson et al. |
| 2003/0105484 A1 | 6/2003 | Boyle et al. | 2003/0208229 A1 | 11/2003 | Kletschka |
| 2003/0105486 A1 | 6/2003 | Murphy et al. | 2003/0208253 A1 | 11/2003 | Beyer et al. |
| 2003/0109824 A1 | 6/2003 | Anderson et al. | 2003/0212428 A1 | 11/2003 | Richter |
| 2003/0109897 A1 | 6/2003 | Walak et al. | 2003/0212429 A1 | 11/2003 | Keegan et al. |
| 2003/0109916 A1 | 6/2003 | Don Michael | 2003/0212431 A1 | 11/2003 | Brady et al. |
| 2003/0114879 A1 | 6/2003 | Euteneuer et al. | 2003/0212432 A1 | 11/2003 | Khairkhahan et al. |
| 2003/0114880 A1 | 6/2003 | Hansen et al. | 2003/0212433 A1 | 11/2003 | Ambrisco et al. |
| 2003/0120303 A1 | 6/2003 | Boyle et al. | 2003/0212434 A1 | 11/2003 | Thielen |
| 2003/0120304 A1 | 6/2003 | Kaganov et al. | 2003/0216774 A1 | 11/2003 | Larson |
| 2003/0125764 A1 | 7/2003 | Brady et al. | 2003/0220665 A1 * | 11/2003 | Eskuri et al. .................. 606/200 |
| 2003/0125765 A1 | 7/2003 | Blackledge et al. | 2003/0220667 A1 | 11/2003 | Van der Burg et al. |
| 2003/0130680 A1 | 7/2003 | Russell | 2003/0225418 A1 | 12/2003 | Esksuri et al. |
| 2003/0130681 A1 | 7/2003 | Ungs | 2003/0225435 A1 | 12/2003 | Hunter et al. |
| 2003/0130682 A1 | 7/2003 | Broome et al. | 2003/0229374 A1 | 12/2003 | Brady et al. |
| 2003/0130684 A1 | 7/2003 | Brady et al. | 2003/0233117 A1 | 12/2003 | Adams et al. |
| 2003/0130685 A1 | 7/2003 | Daniel et al. | 2004/0006364 A1 | 1/2004 | Ladd |
| 2003/0130686 A1 | 7/2003 | Daniel et al. | 2004/0006365 A1 | 1/2004 | Brady et al. |
| 2003/0130687 A1 | 7/2003 | Daniel et al. | 2004/0006370 A1 | 1/2004 | Tsugita |
| 2003/0130688 A1 | 7/2003 | Daniel et al. | 2004/0015152 A1 | 1/2004 | Day |
| 2003/0135232 A1 | 7/2003 | Douk et al. | 2004/0039412 A1 | 2/2004 | Isshiki et al. |
| 2003/0135233 A1 | 7/2003 | Bates et al. | 2004/0049226 A1 | 3/2004 | Keegan et al. |
| 2003/0139764 A1 | 7/2003 | Levinson et al. | 2004/0054394 A1 | 3/2004 | Lee |
| 2003/0139765 A1 | 7/2003 | Patel et al. | 2004/0054395 A1 | 3/2004 | Lee et al. |
| 2003/0144685 A1 | 7/2003 | Boyle et al. | 2004/0059372 A1 | 3/2004 | Tsugita |
| 2003/0144686 A1 | 7/2003 | Martinez et al. | 2004/0064067 A1 | 4/2004 | Ward |
| 2003/0144687 A1 | 7/2003 | Brady et al. | 2004/0064179 A1 | 4/2004 | Linder et al. |
| 2003/0144688 A1 | 7/2003 | Brady et al. | 2004/0068271 A1 | 4/2004 | McAlister |
| 2003/0144689 A1 | 7/2003 | Brady et al. | 2004/0078044 A1 | 4/2004 | Kear |
| 2003/0150821 A1 | 8/2003 | Bates et al. | 2004/0082962 A1 | 4/2004 | Demarais et al. |
| 2003/0153935 A1 | 8/2003 | Mialhe | 2004/0088038 A1 | 5/2004 | Dehnad et al. |
| 2003/0153942 A1 | 8/2003 | Wang et al. | 2004/0093009 A1 | 5/2004 | Denison et al. |
| 2003/0153943 A1 | 8/2003 | Michael et al. | 2004/0093012 A1 | 5/2004 | Cully et al. |
| 2003/0153944 A1 | 8/2003 | Phung et al. | 2004/0093016 A1 | 5/2004 | Root et al. |
| 2003/0153945 A1 | 8/2003 | Patel et al. | 2004/0093059 A1 | 5/2004 | Lee et al. |
| 2003/0158518 A1 | 8/2003 | Schonholz et al. | 2004/0098022 A1 | 5/2004 | Barone |
| 2003/0158574 A1 | 8/2003 | Esch et al. | 2004/0098026 A1 | 5/2004 | Joergensen et al. |
| 2003/0158575 A1 | 8/2003 | Boylan et al. | 2004/0098033 A1 | 5/2004 | Leeflang et al. |
| 2003/0163158 A1 | 8/2003 | White | 2004/0098112 A1 | 5/2004 | DiMatteo et al. |
| 2003/0163159 A1 | 8/2003 | Patel et al. | 2004/0102719 A1 | 5/2004 | Keith et al. |
| 2003/0167068 A1 | 9/2003 | Amplatz | 2004/0106944 A1 | 6/2004 | Daniel et al. |
| 2003/0167069 A1 | 9/2003 | Gonzales et al. | 2004/0116831 A1 | 6/2004 | Vrba |
| 2003/0171769 A1 | 9/2003 | Barbut | 2004/0133232 A1 | 7/2004 | Rosenbluth et al. |
| 2003/0171770 A1 | 9/2003 | Kusleika et al. | 2004/0138696 A1 | 7/2004 | Drasler et al. |
| 2003/0171771 A1 | 9/2003 | Anderson et al. | 2004/0153118 A1 | 8/2004 | Clubb et al. |
| 2003/0171772 A1 | 9/2003 | Amplatz | 2004/0158278 A1 | 8/2004 | Becker et al. |
| 2003/0171800 A1 | 9/2003 | Bicek et al. | 2004/0162576 A1 | 8/2004 | Barbut et al. |
| 2003/0171803 A1 | 9/2003 | Shimon | 2004/0164030 A1 | 8/2004 | Lowe et al. |
| 2003/0176884 A1 | 9/2003 | Berrada et al. | 2004/0167567 A1 | 8/2004 | Cano et al. |

| | | |
|---|---|---|
| 2004/0176794 A1 | 9/2004 | Khosravi |
| 2004/0176833 A1 | 9/2004 | Pavcnik et al. |
| 2004/0199203 A1 | 10/2004 | Oslund et al. |
| 2004/0204737 A1 | 10/2004 | Boismier et al. |
| 2004/0215322 A1 | 10/2004 | Kerr |
| 2004/0225321 A1 | 11/2004 | Krolik et al. |
| 2004/0236369 A1 | 11/2004 | Dubrul |
| 2005/0004663 A1 | 1/2005 | Llanos et al. |
| 2005/0021125 A1 | 1/2005 | Stack et al. |
| 2005/0027345 A1 | 2/2005 | Horan et al. |
| 2005/0038468 A1 | 2/2005 | Panetta et al. |
| 2005/0038503 A1 | 2/2005 | Greenhalgh |
| 2005/0043743 A1* | 2/2005 | Dennis .................. 606/113 |
| 2005/0043756 A1 | 2/2005 | Lavelle et al. |
| 2005/0043780 A1 | 2/2005 | Gifford et al. |
| 2005/0049668 A1 | 3/2005 | Jones et al. |
| 2005/0126979 A1 | 6/2005 | Lowe et al. |
| 2005/0137696 A1 | 6/2005 | Salahieh et al. |
| 2005/0149110 A1 | 7/2005 | Wholey et al. |
| 2005/0165480 A1 | 7/2005 | Jordan et al. |
| 2005/0177186 A1 | 8/2005 | Cully et al. |
| 2005/0177246 A1 | 8/2005 | Datta et al. |
| 2005/0197688 A1 | 9/2005 | Theron et al. |
| 2005/0209634 A1 | 9/2005 | Brady et al. |
| 2005/0216053 A1 | 9/2005 | Douk et al. |
| 2005/0217767 A1 | 10/2005 | Barvosa-Carter et al. |
| 2005/0228474 A1 | 10/2005 | Laguna |
| 2006/0009798 A1 | 1/2006 | Callister et al. |
| 2006/0009799 A1 | 1/2006 | Kleshinski et al. |
| 2006/0020334 A1 | 1/2006 | Lashinski et al. |
| 2006/0030923 A1 | 2/2006 | Gunderson |
| 2006/0074474 A1 | 4/2006 | Theron |
| 2006/0100544 A1 | 5/2006 | Ayala et al. |
| 2006/0100545 A1 | 5/2006 | Ayala et al. |
| 2006/0161241 A1 | 7/2006 | Barbut et al. |
| 2006/0184194 A1 | 8/2006 | Pal et al. |
| 2006/0200221 A1 | 9/2006 | Malewicz |
| 2006/0229660 A1 | 10/2006 | Pal et al. |
| 2006/0264707 A1 | 11/2006 | Kinney |
| 2006/0287668 A1 | 12/2006 | Fawzi et al. |
| 2007/0038241 A1 | 2/2007 | Pal |
| 2007/0100372 A1 | 5/2007 | Schaeffer |
| 2007/0112374 A1 | 5/2007 | Paul, Jr. et al. |
| 2007/0129752 A1 | 6/2007 | Webler et al. |
| 2007/0149996 A1 | 6/2007 | Coughlin |
| 2007/0167974 A1 | 7/2007 | Cully et al. |
| 2007/0185521 A1 | 8/2007 | Bui et al. |
| 2007/0250108 A1 | 10/2007 | Boyle et al. |
| 2007/0288054 A1 | 12/2007 | Tanaka et al. |
| 2008/0015518 A1 | 1/2008 | Huang et al. |
| 2008/0027481 A1 | 1/2008 | Gilson et al. |
| 2008/0103522 A1 | 5/2008 | Steingisser et al. |
| 2008/0154236 A1 | 6/2008 | Elkins et al. |
| 2008/0167629 A1 | 7/2008 | Dann et al. |
| 2008/0255587 A1 | 10/2008 | Cully et al. |
| 2008/0255606 A1 | 10/2008 | Mitra et al. |
| 2008/0262337 A1 | 10/2008 | Falwell et al. |
| 2008/0275569 A1 | 11/2008 | Lesh |

FOREIGN PATENT DOCUMENTS

| | | |
|---|---|---|
| EP | 1127556 A2 | 8/2001 |
| EP | 1 310 219 A2 | 5/2003 |
| EP | 1516601 | 3/2005 |
| EP | 1557137 A1 | 7/2005 |
| WO | WO 92/03097 | 3/1992 |
| WO | WO 96/10591 | 4/1996 |
| WO | WO 99/16382 | 4/1999 |
| WO | WO 99/23976 | 5/1999 |
| WO | WO 99/44510 | 9/1999 |
| WO | WO 01/82831 | 11/2001 |
| WO | WO 03/077799 A2 | 9/2003 |
| WO | WO 2006/138391 A2 | 12/2006 |

OTHER PUBLICATIONS

Heeschen et al., Nature Medicine 7 (2001), No. 7, pp. 833-839.
Johnson et al., Circulation Research 94 (2004), No. 2, pp. 262-268.
International Search Report and Written Opinion for PCT/US2007/020300.
Brochure, "Shuttle Select™ System for Carotid Artery Access," (2004), pp. 1-3.
Brochure, "Slip-Cath® Angiographic Selective Catheters," (2004), pp. 1-6.
Finol, E.A. et al., "Performance Assessment of Embolic Protection Filters for Carotid Artery Stenting," *Modelling in Medicine and Biology IV*, (2005), vol. 8, pp. 133.
Grummon, David S. et al., Appl. Phys. Lett., 82, 2727 (2003), pp. 2727.
Rubicon Embolic Filter, The Next Generation of EM, Rubicon Medical, www.rubiconmed.com, (Jun. 28, 2005).

* cited by examiner

INVERTIBLE FILTER FOR EMBOLIC PROTECTION

CROSS-REFERENCE TO RELATED APPLICATIONS

This application claims the benefit of U.S. Provisional Application Ser. No. 60/727,770, filed on Oct. 18, 2005, entitled "INVERTIBLE FILTER FOR EMBOLIC PROTECTION," the entire contents of which are incorporated herein by reference.

BACKGROUND

1. Field of the Invention

The present invention generally relates to a medical device for embolic protection.

2. Description of Related Art

With the continuing advance of medical techniques, interventional procedures are more commonly being used to actively treat stenosis, occlusions, lesions, or other defects within a patient's blood vessels. Often the treated regions are in the coronary, carotid or even cerebral arteries. One procedure for treating an occluded or stenosed blood vessel is angioplasty. During angioplasty, an inflatable balloon is introduced into the occluded region. The balloon is inflated, pushing against the plaque or other material of the stenosed region and increasing the intralumenal diameter of the vessel. As the balloon presses against the material, portions of the material may inadvertently break free from the plaque deposit. These emboli may travel along the vessel and become trapped in a smaller blood vessel restricting blood flow to a vital organ, such as the brain.

Other methods for removing plaque or thrombus from arteries may include mechanical ablation, or non-contact ablation using light waves, sound waves, ultrasonics, or other radiation. Each of these methods are subject to the risk that some thrombogenic material may dislodge from the wall of the vessel and occlude a smaller blood vessel. The occlusion may cause damage to the patient, including an ischemic stroke in the cerebral arteries.

To prevent the risk of damage from emboli, many devices have been used to restrict the flow of emboli downstream from the stenosed area. One method includes inserting a balloon that may be expanded to occlude the flow of blood through the artery downstream of the stenosed area. An aspirating catheter may be located between the balloon and stenosed area and used to remove emboli that may be caused by the treatment. However, because the balloon completely blocks blood flow through the vessel, the vessel may be occluded only for short periods of time, limiting use of the procedure.

As an alternative to occluding flow through the blood vessel, various filtering devices have been proposed. Such devices typically have elements that form legs or a mesh that would capture embolic material, but allow blood cells to flow between the elements. Capturing the emboli in the filter device prevents the material from being lodged downstream in a smaller blood vessel. The filter may then be removed along with the embolic material after the procedure has been performed and the risk from emboli has decreased.

Challenges also exist with filtering devices. Often it is desirable to deploy filter devices from the proximal side of a stenosis. Therefore, the profile of the filtering device should be significantly smaller than the opening in the stenosed vessel. If the profile of the filtering device is not significantly smaller than the opening, there is an increased risk of dislodging emboli during insertion of the device. Further, if the filter portion is not held against the inside of the vessel wall, there is a risk that embolic material may pass between the filter and the vessel wall. In addition, if the filtering device becomes filled with particles blood flow through the filtering device may be compromised.

In view of the above, it is apparent that there exists a need for an improved medical device for embolic protection.

SUMMARY

In satisfying the above need, as well as overcoming the enumerated drawbacks and other limitations of the related art, the present invention provides an improved medical device for embolic protection. Further, the medical device being applicable to blood vessel, renal, and other applications, similar in nature.

The medical device includes a guiding member and a filter portion. The guiding member includes a lumen configured to slidably engage the filter portion. The filter portion has a tubular geometry that extends distally from the guiding member. The filter portion is configured to evert to form a proximally facing concave geometry for capturing emboli. Further, the filter portion includes filter openings that are sized to allow blood cells to pass therethrough while preventing the passage of emboli. Due to the everted shape, collected emboli arrange themselves in a ring shaped collection area that is spaced from the vessel wall to improve blood flow.

The filter portion may be made of a mesh material having a plurality of interwoven elements. The elements are interwoven such that the filter portion may expand to circumferentially engage the inner wall of the blood vessel when the filter portion is everted. The elements with the mesh material define the filter openings formed in the filter portion. The filter portion including the mesh material may be made of a shape memory alloy to facilitate the everting of the filter portion into the proximally facing concave geometry.

The medical device also includes control wires attached to the filter portion. The control wires may be used to facilitate eversion of the filter material. For example, the core wires may be attached to the distal end of the filter portion and pulled proximally forcing the distal end of the filter portion to evert back over the rest of the filter portion. In addition, the control wires may extend through the tubular geometry to support the filter portion and provide a frame structure for the mesh material. In addition, the control wires may be comprised of a shape memory material and the shape memory characteristics may be used to facilitate eversion or retrieval of the medical device. Further objects, features and advantages of this invention will become readily apparent to persons skilled in the art after a review of the following description, with reference to the drawings and claims that are appended to and form a part of this specification.

DETAILED DESCRIPTION

Figure 1:
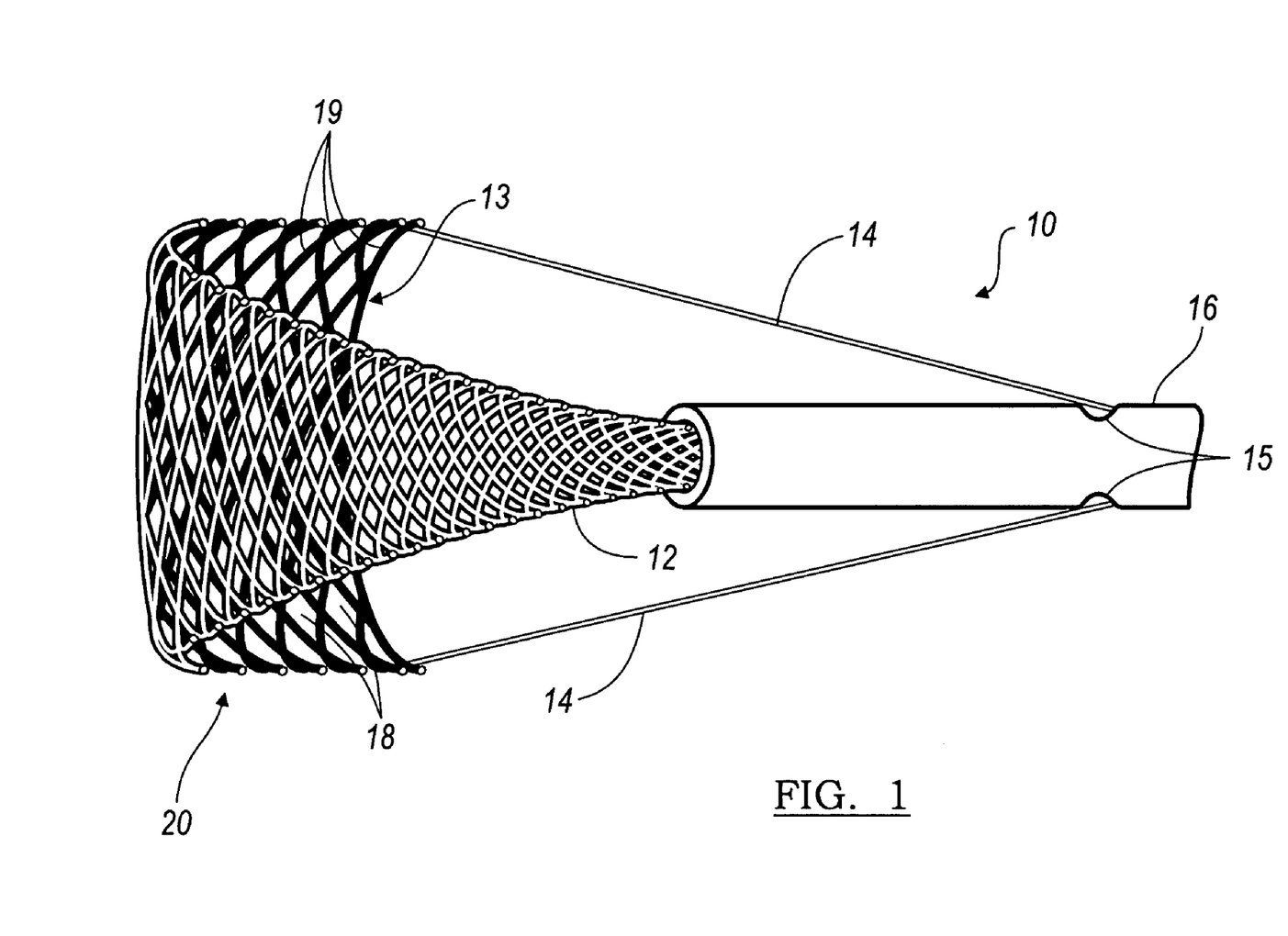
FIG. 1 is a partial sectional view of a medical device in accordance with the present invention.

Referring now to FIG. 1, a medical device embodying the principles of the present invention is denoted by reference numeral 10. The medical device 10 includes a flexible filter portion 12 and a guiding member 16. The filter portion 12 extends distally from the guiding member 16.

In the embodiment shown, the filter portion 12 is made from a mesh material. The mesh material has a tubular geometry including a first opening at the first end 13 of the filter portion 12 and a second opening at the second end of the filter portion 12. The first end 13 extends distally from the guiding member 16 and the second end is engaged by a lumen formed in the guiding member 16. The mesh material includes a plurality of interwoven elements 19. The elements 19 are interwoven such that the diameter of the filter portion 12 can expand or contract while maintaining its generally tubular geometry. To facilitate deployment of the medical device 10, the filter portion 12 may be biased to expand. However, when contracted, the tubular geometry provides a very small profile during insertion of the medical device and facilitates passing the medical device 10 through the stenosis.

The elements 19 may be comprised of any suitable material such as a superelastic material, stainless steel wire, cobalt-chromium-nickel-molybdenum-iron alloy, or cobalt-chrome alloy. Alternatively, the elements 19 may be formed of a synthetic material. For example, Nylon, Dacron, Thorolon, or ePTFE may be used. Depending on the application, the mesh material may include multiple layers or a composite mesh of elements 19, such as a nano fiber mesh. In addition, the elements 19 may include an agent bonded thereto for release in the vessel, such as an anticoagulant. Further, it is understood that the elements 19 may be formed of any other suitable material that will result in a flexible everting geometry, such as shape memory alloys. The mesh material includes openings 18 between the strands that are large enough to allow the flow of blood therethrough, but small enough to capture emboli. Accordingly, the weave of the elements 19 may be configured such that the openings 18 between the strands are between about 30 and 100 microns, although other size openings may be used. Openings of this size in the filter portion 12 will allow blood cells to pass through the openings 18 while larger emboli are constrained by the elements 19.

When deployed, the filter portion 12 is configured to evert thereby forming a proximally facing concave geometry 20. Accordingly, the first end 13 of the filter portion 12 forms a proximally facing opening. The proximally facing concave geometry 20 is adapted to span the diameter of the vessel, such that the filter portion 12 is radially biased against the wall of the vessel. In the everted state, blood flows into the proximally facing opening and through the openings in the mesh material. However, emboli are trapped in the distal most region of the filter portion 12 where the mesh material everts over itself. The distal most portion of the proximally facing concave geometry 20 serves as an annular collection region that is spaced from the wall of the vessel. Accordingly, the emboli form a ring in the annular collection region allowing blood to flow both around the outside and through the middle of the ring.

To control the filter portion 12, the medical device 10 may include control wires 14 attached to the filter portion 12. The control wires 14 may be attached to the filter portion 12 by any suitable means including sonic bonding, thermal bonding, or adhesive bonding. The control wires 14 are moved proximally relative to the guiding member 16 to cause the filter portion 12 to evert. The control wires 14 extends proximally from the first end 13 of the filter portion 12 and are received by the guiding member 16 through control wire openings 15. During retrieval, of the medical device 10 the control wires 14 may be used to pull the filter portion 12 tightly against the guiding member 16, thereby trapping the emboli inside the filter portion 12.

As discussed above, in alternative embodiments the mesh material can be made from a shape memory alloy. Shape memory alloys have the desirable property of becoming rigid, that is, returning to a remembered state, when heated above a transition temperature. A shape memory alloy suitable for the present invention is Ni—Ti available under the more commonly known name Nitinol. When this material is heated above the transition temperature, the material undergoes a phase transformation from martensite to austenite, such that material returns to its. remembered state. The transition temperature is dependent on the relative proportions of the alloying elements Ni and Ti and the optional inclusion of alloying additives.

In one embodiment, the filter portion 12 is made from Nitinol with a transition temperature that is slightly below normal body temperature of humans, which is about 98.6° F. Thus, when the medical device 10 is deployed in a body vessel and exposed to normal body temperature, the alloy of the filter portion 12 will transform to austenite, that is, the remembered state, which for one embodiment of the present invention is the everted state when the filter portion 12 is deployed in the body vessel. To remove the medical device 10, the filter portion 12 is cooled to transform the material to martensite which is more ductile than austenite, making the filter portion 12 more malleable. As such, the medical device 10 can be more easily collapsed and pulled into a lumen of a catheter for removal.

In another alternate embodiment, the filter portion 12 is made from Nitinol with a transition temperature that is above normal body temperature of humans, which is about 98.6°F. Thus, when the medical device 10 is deployed in a body vessel and exposed to normal body temperature, the filter portion 12 is in the martensitic state so that the filter portion 12 is sufficiently ductile to bend or form into a desired shape, which for the present invention is an everted shape. To remove the medical device 10, the filter portion 12 is heated to transform the alloy to austenite so that the medical device becomes rigid and returns to a remembered state, which for the filter portion 12 of this alternate embodiment is a non-everted configuration.

Figure 2:
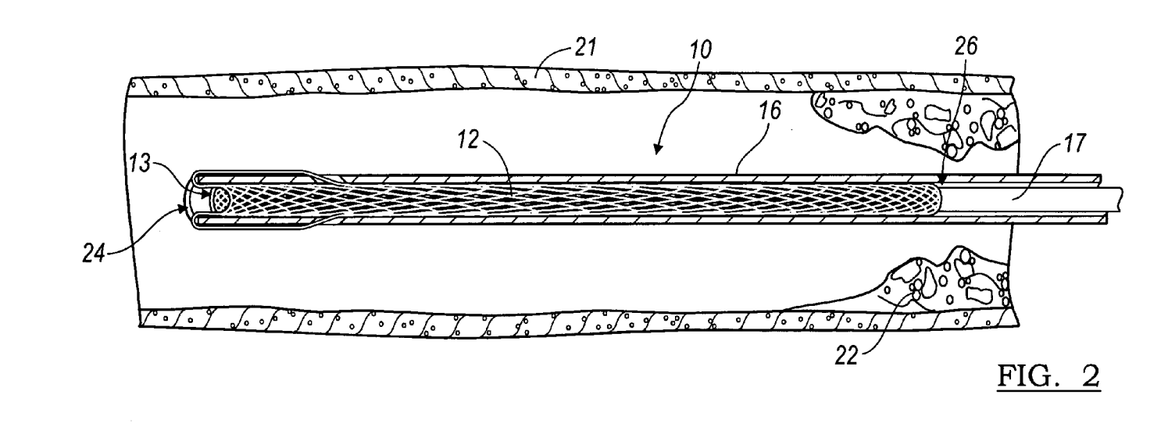
FIG. 2 is a sectional view of a blood vessel including a stenosis and illustrating the introduction of the medical device of FIG. 1, in accordance with the present invention.

Now referring to FIGS. 2-5, a method and system for deploying the medical device 10 is provided. A sectional view of a vessel 21 is provided in FIG. 2, illustrating insertion of the medical device 10. A stenosis 22 is located against the wall of the vessel 21 and would be the subject of an interventional procedure, such as angioplasty, to increase blood flow through the vessel 21. The medical device 10 can be deployed to contain emboli that may break free from the stenosis 22 during the interventional procedure.

The medical device 10 is advanced through the blood vessel 21 distal the stenosis 22. The filter portion 12 is contained within the guiding member 16 along with an advancement member 17. The second end of filter portion 12 is attached to the distal end 26 of advancement member 17 through any suitable means including sonic bonding, thermal bonding, or adhesive bonding. While contained within the guiding member 16, the tubular geometry of the filter portion 12 is collapsed allowing the guiding member 16 to retain a very small profile. As previously mentioned, maintaining a small profile reduces the risk of dislodging emboli during deployment of the medical device 10.

Figure 3:
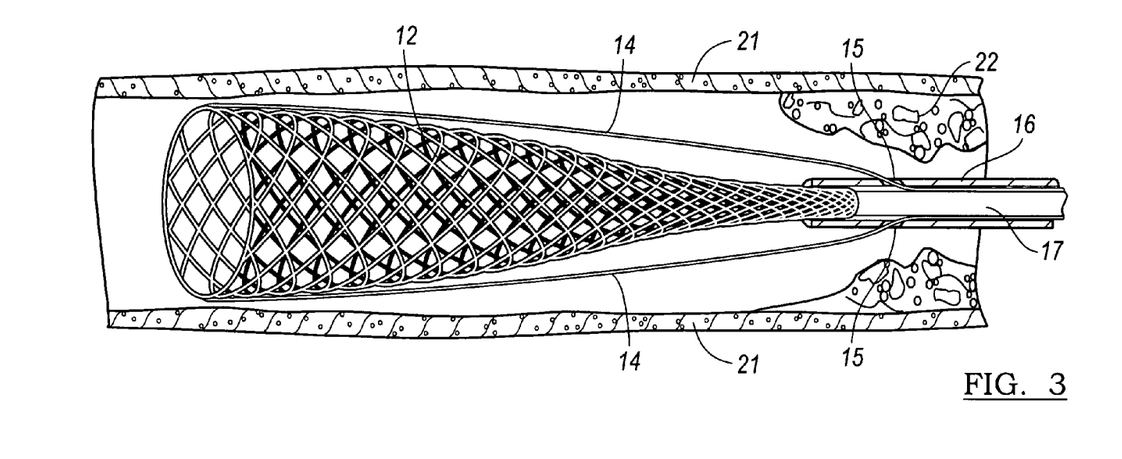
FIG. 3 is a sectional view of the blood vessel illustrating deployment of the medical device in FIG. 1.

Now referring to FIG. 3, the advancement member 17 is moved distally relative to the guiding member 16, such that the filter portion 12 extends from the distal end 24 of the guiding member 16. As the filter portion 12 is advanced from the guiding member 16, the filter portion 12 may be biased to expand while retaining its tubular geometry.

Figure 4:
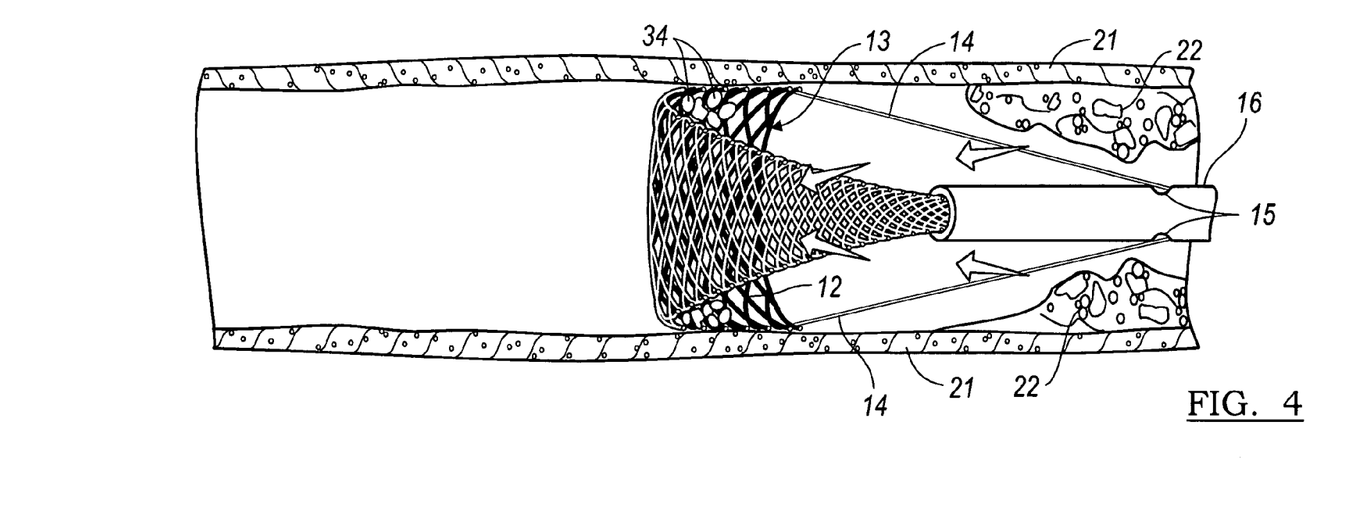
FIG. 4 is a sectional view of the blood vessel illustrating the medical device of FIG. 1 in a fully deployed state.

Now referring to FIG. 4, the filter portion is then everted to form a proximally facing concave geometry. The filter portion 12 may be everted by moving the control wires 14 proximally, thereby pulling the first end 13 of the filter portion 12 back over the rest of the filter portion 12. Further, the filter portion 12 may also be made of a shape memory material such that the filter portion 12 has two defined geometries. For example, the mesh material may be made of a shape memory alloy so that the mesh material 20 is biased into a straight tubular geometry in a non-everting state at a first temperature. The first temperature being controlled, for example, by fluid flowing through the guiding member 16 across the medical device 10. At a second temperature, such as the ambient temperature inside the vessel 21, the filter portion 12 is biased into a proximally facing concave geometry. When the filter portion 12 is biased into the proximally facing concave geometry, the filter portion 12 everts causing the filter portion 12 to expand against the inner wall of the vessel 21. While the medical device 10 is expanded against the inner wall of the vessel 21, the filter portion 12 serves to collect emboli that may break free from the stenosed area preventing such emboli from blocking smaller vessels downstream of the medical device 10.

Figure 5:
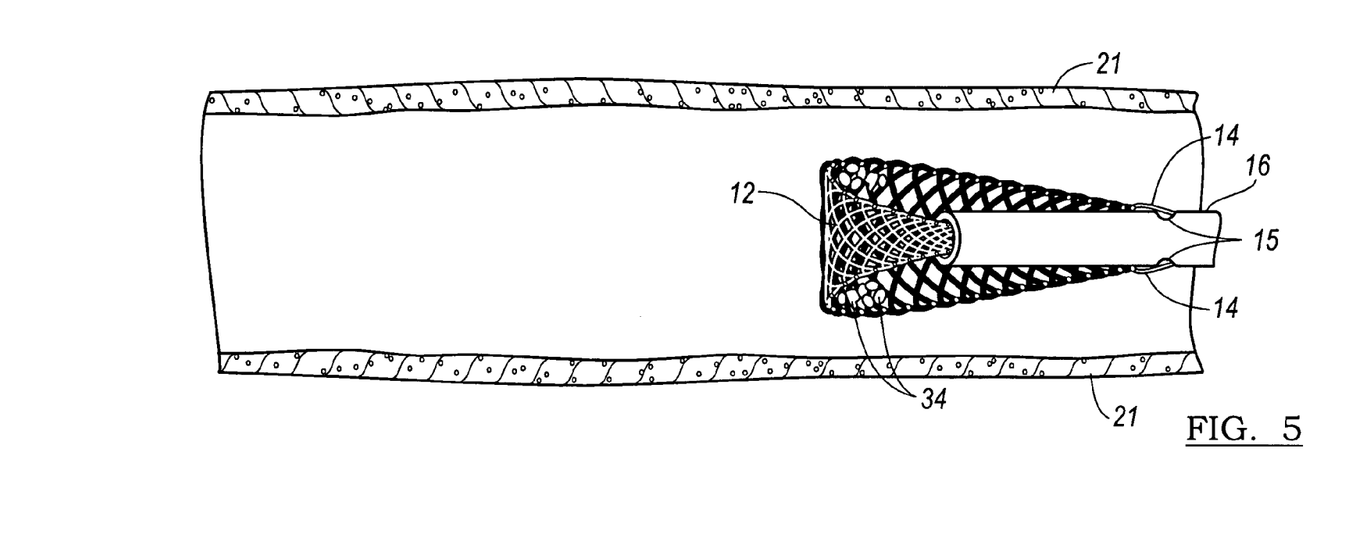
FIG. 5 is a sectional view of the blood vessel illustrating the medical device prior to removal.

When everted, the first end 13 of the filter portion 12 is biased against the inner wall of the vessel 21 forcing the fluid to flow through the proximally facing concave geometry formed by the filter portion 12. Therefore, emboli 34 are trapped in the distal region of the proximally facing concave geometry. The medical device 10 remains in this expanded state during the interventional procedure to capture any emboli that break free from the stenosis 22. After the interventional procedure is completed, the medical device 10 may be removed as shown in FIG. 5. To trap the emboli 34 in the filter portion 12, the control wires 14 may be pulled further proximally drawing the filter portion 12 against the guiding member 16.

Figure 6:
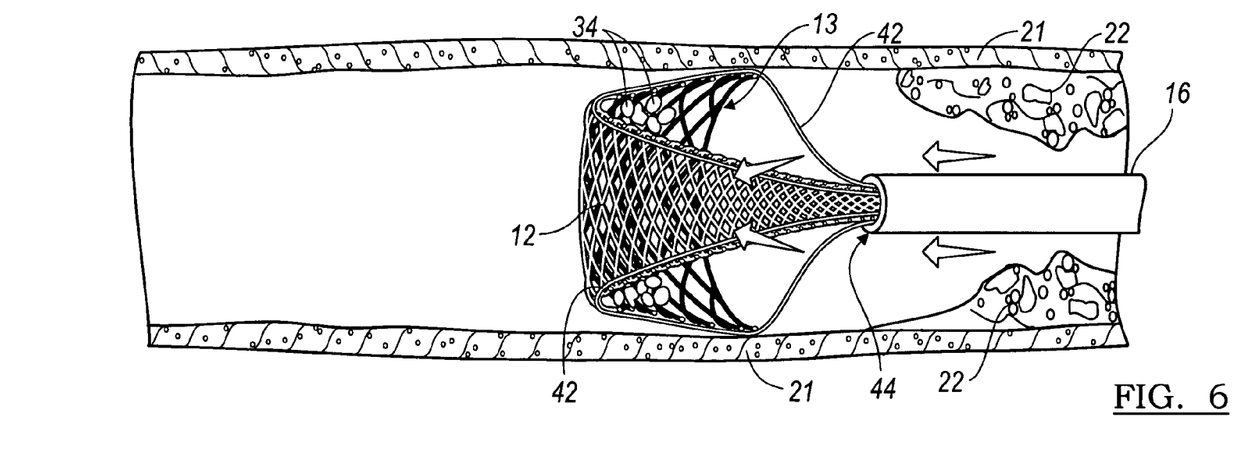
FIG. 6 is a sectional view of a blood vessel illustrating another embodiment of a medical device in accordance with the present invention.

Another embodiment of the present invention is shown in FIG. 6. The medical device 40 is depicted with a guiding member 16 and filter portion 12 as described above in connection with the medical device 10. However, the control wires 42 extend through the tubular geometry of the filter portion 12. Accordingly, the control wires 42 form a frame structure along the length of the filter portion 12. The control wires 42 may be made of a synthetic material, a stainless steel, or a shape memory alloy, such as Nitinol. The shape memory characteristics of the control wire 42 may be used to support the first end 13 of the filter portion 12 against the inner wall of the vessel 21. Supporting the filter portion 12 against the wall of the vessel ensures that the fluid will flow through the proximally facing concave geometry formed by the everted filter portion 12, thereby causing emboli to be trapped by the medical device 40.

If the control wires 42 are made of a shape memory material, the control wires 42 may have a low profile geometry defined at a first temperature and an expanded geometry defined at a second temperature. Accordingly, the first temperature inside the guiding member 16 may be controlled to maintain a non-everted state. For example, a fluid may be passed through the guiding member to manipulate the temperature of the control wires 42 thereby controlling the state of the shape memory material in the control wires 42. As the medical device 40 is pushed out of the distal opening 44 of the guiding member 16, the temperature of the shape memory material of the control wire will change according to the temperature of the vessel 21. The second temperature inside the vessel 21 causes the control wires 42 to force outwardly against the inner wall of the vessel 21.

Figure 7:
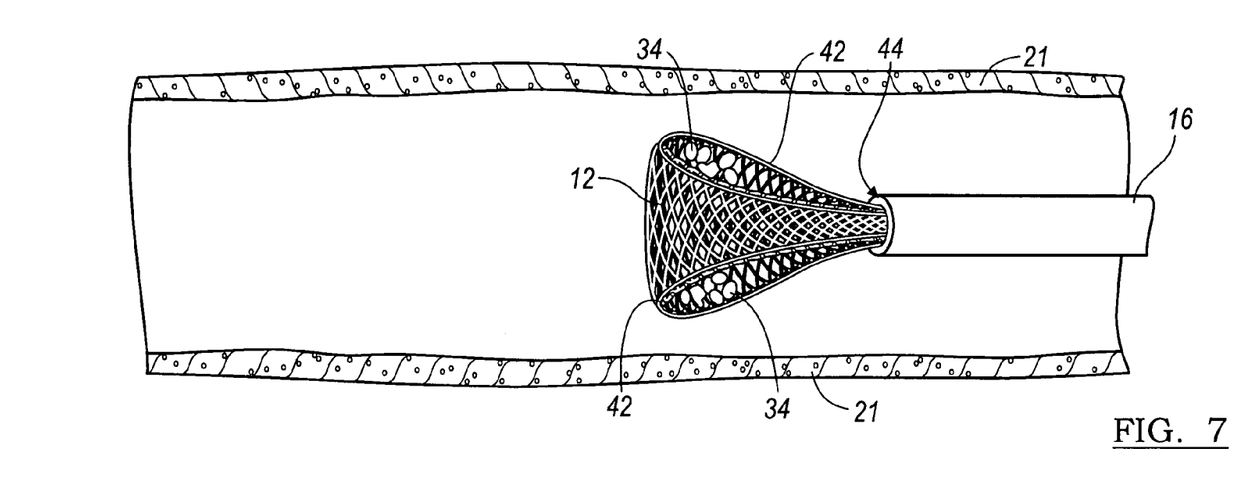
FIG. 7 is a sectional view of the blood vessel illustrating the medical device of FIG. 6 prior to removal.
Figure 8:
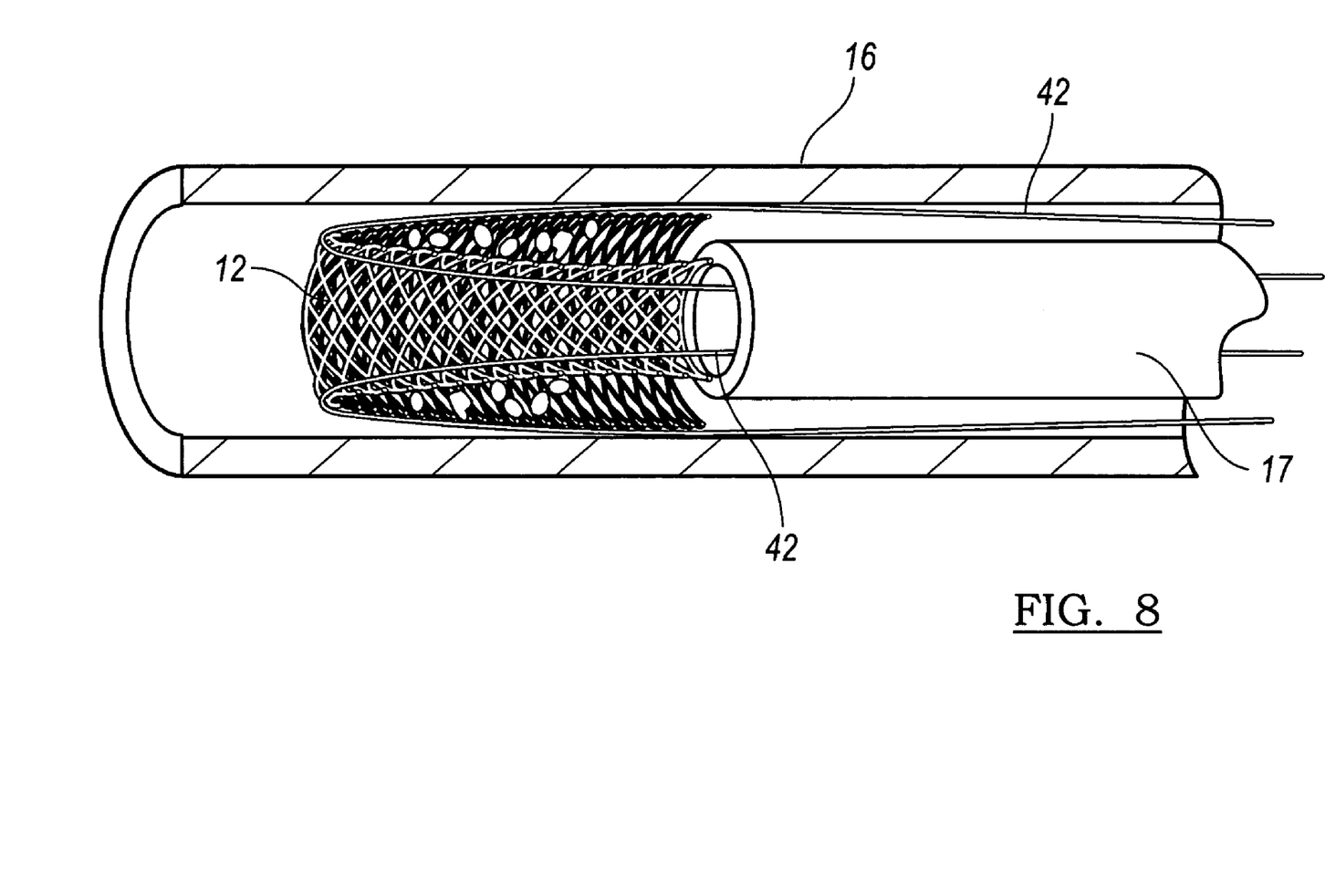
FIG. 8 is a sectional view of a the medical device of FIG. 6 during removal from the vessel.

In addition, the control wires 42 extend from the first end 13 of the filter portion 12 through the distal opening 44 in the guiding member 16. Accordingly, no control wire openings are provided in the guiding member 16 as were provided with previous embodiment of the medical device 10. After the interventional procedure is complete, the medical device 40 may be removed from the vessel 21. To trap emboli 34 in the filter portion 12 the control wires 42 are pulled proximally into the guiding member 16. Accordingly, the first end 13 of the filter portion may also be pulled into the guiding member 16 thereby sealing the emboli 34 within the filter portion 12. To further secure the emboli within the medical device 40, the guiding member 16 may be configured to retract the entire filter portion and emboli 34 within the guiding member lumen 46 prior to removal from the vessel.

As a person skilled in the art will readily appreciate, the above description is meant as an illustration of implementation of the principles this invention. This description is not intended to limit the scope or application of this invention in that the invention is susceptible to modification, variation and change, without departing from spirit of this invention, as defined in the following claims.

We claim:

1. A medical device for capturing emboli in a blood vessel, the medical device comprising:
   a guiding member including a lumen sized to receive an advancement member, an outer surface, a distal end, and a plurality of control wire openings proximal to the distal end;
   a filter portion having a tubular geometry and a plurality of filter openings, the tubular geometry having a first end opening at a first end and a second end opening at a second end, the first end extending distally from the guiding member, the second end being fixedly attached to the advancement member;
   a plurality of control wires attached to the filter portion and extending proximally from the first end of the filter portion, wherein the plurality of control wires are received into the lumen of the guiding member through the plurality of control wire openings; and
   wherein the filter portion has a non-everted state and an everted state, the filter portion being configured to evert by pulling the first end back over the filter portion so that the filter portion forms a proximally facing concave geometry with the first end forming a proximally facing opening; and
   wherein the everted state of the filter portion has an expanded state and a collapsed state, wherein the first end of the filter portion is drawn against the outer surface of the guiding member by proximal movement of the control wires and the second end of the filter portion is disposed within the lumen of the guiding member when the filter portion is in the collapsed state, such that the distal end of the guiding member is disposed within the concave geometry of the filter portion when the filter portion is in the collapsed state.

2. The medical device according to claim 1, wherein the filter portion includes a plurality of elements, the elements being interwoven such that the filter portion expands to circumferentially engage an inner wall of the blood vessel when everted.

3. The medical device according to claim 2, wherein the plurality of elements define the plurality of filter openings.

4. The medical device according to claim 3, the plurality of filter openings are sized to allow blood cells to pass through the filter openings and prevent the passage of emboli.

5. The medical device according to claim 1, wherein the filter portion is comprised of a shape memory material.

6. The medical device according to claim 1, wherein the plurality of control wires are comprised of a shape memory material.

7. The medical device according to claim 1, wherein the proximally facing concave geometry has an annular collection region.

8. The medical device according to claim 7, wherein the annular collection region is spaced from the blood vessel.

9. A medical device for capturing emboli in a blood vessel, the medical device comprising:
 a guiding member including a lumen sized to receive an advancement member, an outer surface, a distal end, and a plurality of control wire openings proximal to the distal end;
 a filter portion having a tubular geometry and a plurality of filter openings, the tubular geometry having a first and second end, the first end extending distally from the guiding member; the second end being fixedly attached to the advancement member;
 a plurality of control wires attached to the filter portion and extending proximally from the first end of the filter portion, wherein the plurality of control wires are received into the lumen of the guiding member through the plurality of control wire openings; and
 wherein the filter portion has a non-everted state and an everted state, the filter portion being configured to evert by proximal movement of the control wires, the proximal movement of the control wires pulling the first end back over the filter portion so that the filter portion forms a proximally facing concave geometry with the first end forming a proximally facing opening, the filter portion including a plurality of elements interwoven such that the filter portion expands to circumferentially engage an inner wall of the blood vessel when everted, the plurality of elements defining the plurality of filter openings; and
 wherein the everted state of the filter portion has an expanded state and a collapsed state, wherein the first end of the filter portion is drawn against the outer surface of the guiding member by proximal movement of the control wires and the second end of the filter portion is disposed within the lumen of the guiding member when the filter portion is in the collapsed state, such that the distal end of the guiding member is disposed within the concave geometry of the filter portion when the filter portion is in the collapsed state.

10. The medical device according to claim 9, the plurality of filter openings are sized to allow blood cells to pass through the filter openings and prevent the passage of emboli.

11. The medical device according to claim 9, wherein the filter portion is comprised of a shape memory material.

12. The medical device according to claim 9, wherein the plurality of control wires are comprised of a shape memory material.

13. The medical device according to claim 9, wherein the proximally facing concave geometry has an annular collection region and the annular collection region is spaced from the blood vessel.

* * * * *